US012746407B2

(12) United States Patent
Haase

(10) Patent No.: US 12,746,407 B2
(45) Date of Patent: Sep. 29, 2026

(54) HIGH-INTENSITY FOCUSED ELECTROMAGNETIC THERAPY FOR HYPOGONADISM AND ASSOCIATED SYSTEMS

(71) Applicant: Agileworks LLC, Alexandria, VA (US)

(72) Inventor: Jonathan Haase, Alexandria, VA (US)

(73) Assignee: AGILEWORKS LLC, Alexandria, VA (US)

( * ) Notice: Subject to any disclaimer, the term of this patent is extended or adjusted under 35 U.S.C. 154(b) by 223 days.

(21) Appl. No.: 18/791,259

(22) Filed: Jul. 31, 2024

(65) Prior Publication Data

US 2025/0041616 A1 Feb. 6, 2025

Related U.S. Application Data

(60) Provisional application No. 63/530,017, filed on Jul. 31, 2023.

(51) Int. Cl.
*A61N 1/40* (2006.01)

(52) U.S. Cl.
CPC ...................................... *A61N 1/40* (2013.01)

(58) Field of Classification Search
CPC ..... A61N 1/40; A61N 1/0524; A61N 1/36007
See application file for complete search history.

(56) References Cited

U.S. PATENT DOCUMENTS

| | | | | |
|---|---|---|---|---|
| 5,984,854 A * | 11/1999 | Ishikawa | A61N 2/02 | |
| | | | 600/9 | |
| 12,076,575 B2 * | 9/2024 | Mizrahy | A61N 1/403 | |
| 2016/0082180 A1 * | 3/2016 | Toth | A61M 5/14 | |
| | | | 604/21 | |
| 2022/0296910 A1 * | 9/2022 | Mizrahy | A61N 1/403 | |
| 2023/0001205 A1 * | 1/2023 | Aprasoff | A61N 1/36003 | |

FOREIGN PATENT DOCUMENTS

| | | | | |
|---|---|---|---|---|
| CN | 1568919 A | 1/2005 | | |
| CN | 107469242 A | 12/2017 | | |
| CN | 212941015 U * | 4/2021 | | |
| CN | 113648203 A | 11/2021 | | |
| EP | 0788813 B1 | 10/2003 | | |
| RU | 2766735 C1 | 3/2022 | | |
| WO | WO-2011013974 A2 * | 2/2011 | A47K 13/24 | |

OTHER PUBLICATIONS

PCT/US2024/040463 International Search Report and Written Opinion dated Nov. 20, 2024; 12 pages.

* cited by examiner

*Primary Examiner* — Jonathan T Kuo
(74) *Attorney, Agent, or Firm* — McCoy Russell LLP

(57) ABSTRACT

Embodiments provide a device for treating hypogonadism, the device including: a seat, where the seat includes a pair of longitudinal grooves, and a pair of applicators. Each applicator is configured to deliver HIFEM energy and RF energy. The pair of longitudinal grooves are configured to engage the pair of applicators, where the applicators are slidably engaged to move along the longitudinal grooves from a disengaged position to an engaged position against a patient's body for treating hypogonadism. The pair of applicators includes a front applicator configured to engage a patient's penis and a front portion of the patient's pelvic floor and a rear applicator configured to engage a patient's anus and a rear portion of the patient's pelvic floor, in the engaged position. When in the engaged position, the front applicator and the rear applicator are configured to deliver the HIFEM and RF energies to the patient's pelvic floor muscles for treating the patient's hypogonadism.

16 Claims, 7 Drawing Sheets

HIGH-INTENSITY FOCUSED ELECTROMAGNETIC THERAPY FOR HYPOGONADISM AND ASSOCIATED SYSTEMS

CROSS REFERENCE TO RELATED APPLICATION

This application claims priority to U.S. Provisional Patent Application Ser. No. 63/530,017, filed on Jul. 31, 2023, which is hereby incorporated by reference in its entirety into this application.

BACKGROUND

Field

Embodiments generally relate to a device for treating hypogonadism using High-Intensity Focused Electromagnetic (HIFEM) therapy and optionally Radio Frequency (RF) therapy. More particularly, the device applies HIFEM and RF therapies to the pelvic floor muscles of a patient experiencing hypogonadism, aiming to enhance the strength and functionality of the pelvic floor muscles and improve blood circulation to the testes and penis. According to various embodiments, the device can be used with any existing HIFEM/RF system and is designed for clinical use.

Description of the Related Art

Hypogonadism, a condition characterized by reduced testosterone production, affects numerous men globally. This condition can arise for various reasons, including testicular dysfunction, pituitary gland issues, or hypothalamus irregularities. Symptoms of hypogonadism can range from reduced libido, erectile dysfunction, fatigue, muscle weakness, and mood disturbances.

Hypogonadism affects a significant portion of the male population, and the current treatment options include:

(1) Testosterone Replacement Therapy (TRT): The most common TRT treatment involves direct testosterone supplementation. While effective for many, it has potential side effects and doesn't address the root causes of reduced testosterone production. Additionally, not all patients are suitable candidates for TRT and some may not achieve the desired therapeutic benefits.

(2) Selective Estrogen Receptor Modulators (SERMs): SERMs can increase testosterone production by acting on the pituitary gland, but can have side effects.

(3) Human Chorionic Gonadotropin (hCG) Injections: hCG injections can stimulate the testes to produce more testosterone. However, regular injections are needed.

(4) Lifestyle Changes: Diet, exercise, and stress management can help improve testosterone levels, but they require sustained effort and might not be sufficient for all affected individuals.

Conventional treatments for hypogonadism do not contemplate the use of HIFEM therapy. In some cases, conventional treatments for chronic prostatitis complicated by erectile dysfunction use high intensity pulsed magnetic fields (HI-PEMF), which a medical professional treating hypogonadism would understand are different forms of electromagnetic energy and used for different purposes. For example, HI-PEMF involves the use of strong electromagnetic fields that are powered by brief pulses of electric current, producing a brief but strong pulse of magnetic field. These pulsed magnets can generate stronger fields than continuous magnets.

What is needed is a non-pharmacological, non-invasive, and a more effective solution for managing hypogonadism and its associated symptoms.

SUMMARY

Embodiments address the need for a more effective solution for managing hypogonadism and erectile dysfunction and its associated symptoms by harnessing the potential of HIFEM therapy and optionally, in some embodiments, the inclusion of RF therapy. The primary objective of various embodiments is to increase the strength of the pelvic floor muscles while increasing blood flow to the testes. The increased blood flow to the testes and penis during the HIFEM therapy (and optionally RF therapy) will help heal and rejuvenate the testes, increasing testosterone. The increased strength of the pelvic floor muscles will improve blood flow to the testes after treatment. The effect stimulates the testes and associated endocrine structures, potentially enhancing testosterone production naturally. By doing so, this method offers a promising avenue for treating hypogonadism without the complications linked with conventional therapies.

According to an embodiment, there is provided a device for treating hypogonadism, the device including a seat, where the seat includes a pair of longitudinal grooves, and a pair of applicators. Each applicator is configured to deliver HIFEM energy and RF energy. The pair of longitudinal grooves are configured to engage the pair of applicators, where the applicators are slidably engaged to move along the longitudinal grooves from a disengaged position to an engaged position against a patient's body for treating hypogonadism. The pair of applicators includes a front applicator configured to engage a patient's penis and a front portion of the patient's pelvic floor and a rear applicator configured to engage a patient's anus and a rear portion of the patient's pelvic floor, in the engaged position. When in the engaged position, the front applicator and the rear applicator are configured to deliver the HIFEM and RF energies to the patient's pelvic floor muscles for treating the patient's hypogonadism.

According to an embodiment, the seat further includes a seat applicator, the seat applicator being configured to deliver HIFEM and RF energies.

According to an embodiment, when the device is in the engaged position, the seat applicator is configured to deliver the HIEFM and RF energies to the patient's pelvic floor muscles for treating the patient's hypogonadism.

According to an embodiment, the seat applicator, the front applicator and the rear applicator are each configured to deliver the HIFEM and RF energies concurrently to the muscles and fat tissues of the patient's pelvic floor muscles.

According to an embodiment, the seat applicator, the front applicator, and the rear applicator are each configured to concurrently deliver the HIFEM energy pulsed at between 1 Hz to 500 Hz with a continuous application of RF energy in the range of 1 MHz to 3 MHz.

According to an embodiment, the device further includes a control panel including a patient-operated button configured to terminate the delivery of the HIFEM and RF energies, when the patient experiences discomfort during treatment.

According to an embodiment, the seat applicator, the front applicator, and the rear applicator are each configured to deliver the HIFEM energy and RF energy for a duration of 10 to 30 minutes long, depending on the patient's comfort level.

According to an embodiment, the front applicator and the rear applicator are designed to accommodate the contour of the male pelvic area, ensuring accurate positioning and delivery of focused electromagnetic waves to the patient's testicular region and boosting testosterone.

According to an embodiment, the device further includes a safety cutoff switch, operated by the patient, configured to modulate the treatment intensity within the tolerances of the patient's treatment comfort.

According to another embodiment, there is provided a method for treating hypogonadism. The method uses a device including a seat, where the seat includes a pair of longitudinal grooves, and a pair of applicators. Each applicator is configured to deliver HIFEM energy and RF energy. The pair of longitudinal grooves are configured to engage the pair of applicators, where the applicators are slidably engaged to move along the longitudinal grooves from a disengaged position to an engaged position against a patient's body for treating hypogonadism. The pair of applicators includes a front applicator configured to engage a patient's penis and a front portion of the patient's pelvic floor and a rear applicator configured to engage a patient's anus and a rear portion of the patient's pelvic floor, in the engaged position. When in the engaged position, the front applicator and the rear applicator are configured to deliver the HIFEM and RF energies to the patient's pelvic floor muscles for treating the patient's hypogonadism. The method includes the steps of:

According to an embodiment, the method further includes the steps of: engaging the other of the front applicator and the rear applicator in a direction towards the patient's pelvic region, generating the HIFEM and RF energies using HIFEM and RF generators, delivering, when the other of the front applicator and the rear applicator is engaged with the patient, the HIFEM energy from the other engaged applicator to the patient's pelvic floor muscles, concurrently delivering the RF energy from the other engaged applicator to the patient's pelvic floor muscles, and adjusting the intensity of the delivering of the HIFEM energy and the RF energy based on the patient's comfort to treat the patient's hypogonadism.

According to an embodiment, the seat further includes a seat applicator, the seat applicator being configured to deliver HIFEM and RF energies, and the method further including the steps of delivering, from the seat applicator, the HIFEM energy to the patient's pelvic floor muscles, concurrently delivering the RF energy from the seat applicator to the patient's pelvic floor muscles, and adjusting the intensity of the delivering of the HIFEM energy and the RF energy based on the patient's comfort to treat the patient's hypogonadism.

According to an embodiment, the step of delivering includes delivering the HIFEM and RF energies concurrently to the muscles and fat tissues of the patient's pelvic floor muscles.

According to an embodiment, the seat applicator, the front applicator, and the rear applicator are each configured to concurrently deliver the HIFEM energy pulsed at between 1 Hz to 500 Hz with a continuous application of RF energy in the range of 1 MHz to 3 MHz.

According to an embodiment, the device further includes a control panel comprising a patient-operated button, and the method further includes the step of terminating, using the patient-operated button, the delivery of the HIFEM and RF energies, when the patient experiences discomfort during treatment.

According to an embodiment, the seat applicator, the front applicator, and the rear applicator are each configured to deliver the HIFEM energy and RF energy for a duration of 10 to 30 minutes long, depending on the patient's comfort level.

According to an embodiment, the front applicator and the rear applicator are designed to accommodate the contour of the male pelvic area, ensuring accurate positioning and delivery of focused electromagnetic waves to the patient's testicular region and boosting testosterone.

BRIEF DESCRIPTION OF THE DRAWINGS

So that the manner in which the recited features, aspects and advantages of the disclosure, as well as others that will become apparent, are attained and can be understood in detail, a more particular description of certain embodiments briefly summarized above can be had by reference to the embodiments that are illustrated in the drawings that form a part of this specification. It is to be noted, however, that the appended drawings illustrate only exemplary embodiments and are, therefore, not to be considered limiting of the disclosure's scope, for the disclosure can admit to other equally effective embodiments. Like numbers refer to like elements throughout, and the prime notation, if used, indicates similar elements in alternative embodiments or positions.

FIG. 5A is a top view of the device with the front applicator and rear applicator moving into an engaged position to the patient's body; FIG. 5B is a side view of the device with the front applicator moving into an engaged position to the patient's body and a rear applicator engaged with the rear torso of the patient;

FIG. 5C is a side view of the device with the front applicator and the rear applicator engaged with the front and rear torso of the patient, according to an embodiment, respectively.

DETAILED DESCRIPTION

Figure 1:
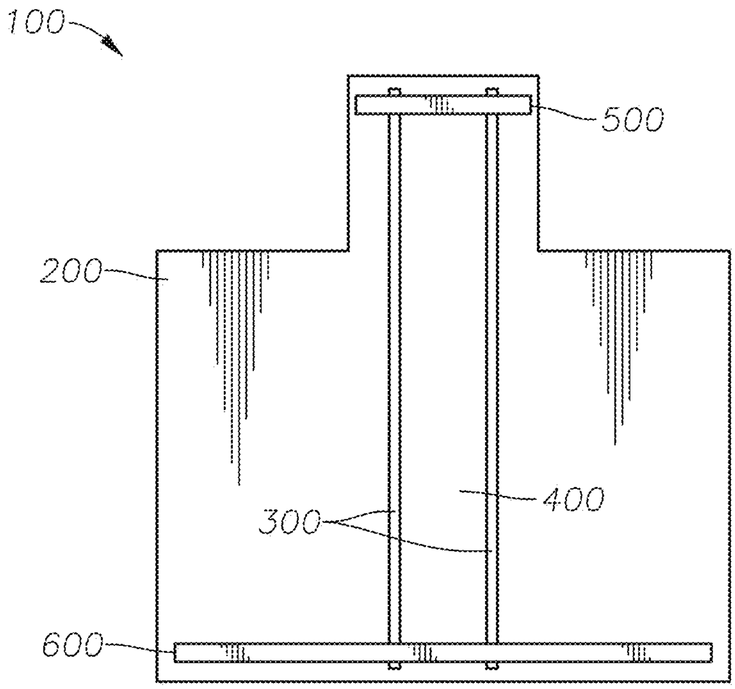
FIG. 1 is a top schematic view of a device for treating hypogonadism using HIFEM/RF energies, according to an embodiment.

While the scope of the system and method will be described with several embodiments, it is understood that one of ordinary skill in the relevant art will appreciate that many examples, variations and alterations to the systems and methods described here are within the scope and spirit of the embodiments.

Accordingly, the embodiments described are set forth without any loss of generality, and without imposing limitations, on the embodiments. Those of skill in the art understand that the scope includes all possible combinations and uses of particular features described in the specification.

Embodiments provide a device have a set of bespoke HIFEM/RF applicators tailored for the male anatomy, aiming to ensure efficient, comfortable, and safe clinical procedures. The device, and associated method, addresses hypogonadism and erectile dysfunction by harnessing the capabilities of HIFEM and RF therapies. Instead of solely focusing on direct testosterone replacement, embodiments acknowledge the multifaceted nature of hypogonadism and seek to address it from a physiological perspective. HIFEM therapy leverages electromagnetic energy to induce powerful contractions in the pelvic floor muscles. The strengthening of these muscles will enhance blood flow to the testes and penis, creating an environment conducive to optimal testosterone production. By focusing on this physiological pathway, embodiments offer a unique and innovative means to potentially augment natural testosterone synthesis, providing a non-invasive and holistic alternative to traditional treatments.

The HIFEM applicators integrated into the device, according to an embodiment, enables the operator to directly target the root causes of hypogonadism. Specifically, they aim to stimulate natural testosterone production while also addressing factors that may influence testosterone levels, such as body fat percentage, or improving the health and function of the associated endocrine structures.

Unlike TRT, which offers exogenous testosterone without addressing the body's natural production mechanisms, the device, according to embodiments, uses HIFEM technology to potentially stimulate endogenous testosterone production.

In contrast to SERMs and hCG, which chemically induce testosterone production, the device, according to embodiments, offers a non-pharmacological approach, potentially reducing associated side effects.

Unlike lifestyle changes, which require continuous effort and may not be effective for everyone, the device, according to embodiments, provides a direct and targeted intervention that can be clinically administered in a safe, effective, and comfortable setting.

In contrast to HI-PEMF, the device, according to embodiments, uses HIFEM therapy to apply electromagnetic stimulation to contract the muscles in a targeted area. These magnetic fields create electrical currents, which are passed to the muscles. When these magnetic pulses are fast enough, they force the muscles to contract, much like they do during times of strenuous exercise. Therefore, when the muscles contract enough times, they begin to build muscles and burn fat.

Thus, the device, according to embodiments, presents a holistic approach to treating hypogonadism, addressing the root causes typically overlooked by conventional treatments. It signifies a notable advancement over existing solutions in the field. The device provides a novel approach for applying frequency, power, and duration of HIFEM energy, and optionally RF energy, necessary to effectively raise testosterone levels, thereby providing the patient with an adaptable, safe, and comfortable treatment for hypogonadism.

As used in this application, conventional HIFEM machines utilize electromagnetic energy to target skeletal muscle. Such stimulation has potential implications for boosting testosterone levels naturally, addressing the primary concern of hypogonadism. Furthermore, integrating RF energy can further optimize the therapeutic potential of various embodiments of the claimed device. RF therapy has shown efficacy in fat reduction and tissue remodeling. Given that body fat percentage can influence testosterone levels, reducing excess adipose tissue can contribute to the normalization of testosterone levels. In addition, removing fat from the pelvis can increase the available space for the vasculature of the pelvis.

In the context of hypogonadism, where diminished testosterone can lead to symptoms, such as reduced libido, fatigue, and mood disturbances, the combined application of HIFEM and RF therapies can offer a comprehensive approach to treatment.

Adipose tissue plays a pivotal role in male endocrine health. Fat cells contain the enzyme aromatase, which converts testosterone to estradiol, a form of estrogen. An excess of adipose tissue can lead to higher aromatase activity, reducing the availability of testosterone. This can disrupt the balance of male hormones and contribute to the symptoms of hypogonadism. The device and method, according to embodiments, reduces the fat in the pelvic floor and groin region, leading to less aromatase.

The multifaceted nature of testosterone production and regulation underscores the need for a holistic approach to treating hypogonadism. The disorder can arise due to issues within the HPG axis, imbalances in hormone conversion due to excessive adipose tissue, or a combination of factors. A comprehensive approach, such as utilizing HIFEM therapy, might offer a promising treatment strategy. By muscle growth in the pelvic floor and increasing blood flow to the groin as well as reducing excess adipose tissue, the device and method, according to embodiments, provides a comprehensive, drug-free approach to address hypogonadism.

Figure 2:
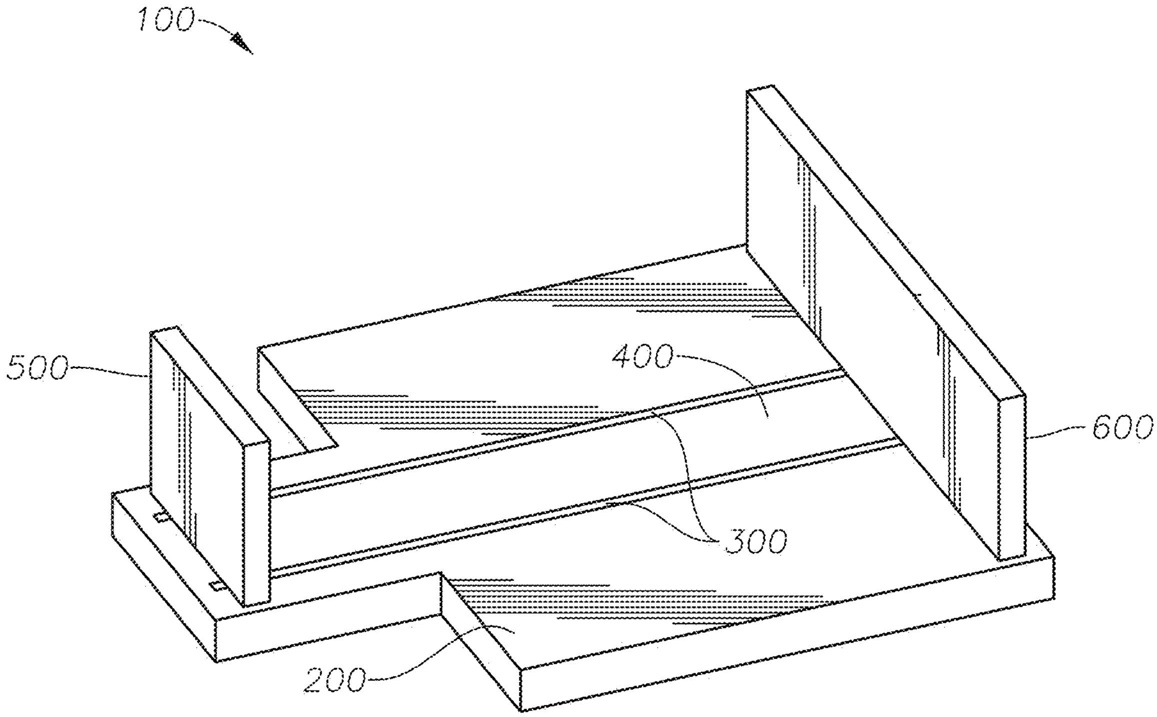
FIG. 2 is a side view of the device for treating hypogonadism using HIFEM/RF energies, in a disengaged position, according to an embodiment.

Referring now to the disclosed devices in more detail, FIG. 1 is a top schematic view of a device 100 for treating hypogonadism using HIFEM/RF energy, according to an embodiment, and FIG. 2 is a side view of the device 100 for treating hypogonadism using HIFEM/RF energy, in a disengaged position, according to an embodiment.

As shown in FIGS. 1 and 2, the device 100 includes a seat 200 having a pair of longitudinal grooves 300, and a pair of applicators 500, 600, each applicator configured to deliver High-Intensity Focused Electromagnetic Technology (HIFEM) energy and Radio Frequency (RF) energy. The pair of longitudinal grooves 300 are configured to engage the pair of applicators 500, 600, where the applicators 500, 600 are slidably engaged to move along the longitudinal grooves 300 from a disengaged position to an engaged position against a patient's body for treating hypogonadism. Furthermore, the pair of applicators 500, 600 includes a front applicator 500 configured to engage a patient's penis and a front portion of the patient's pelvic floor and a rear applicator 600 configured to engage a patient's anus and a rear portion of the patient's pelvic floor, in the engaged position. According to an embodiment, the seat 200 further includes a seat applicator 400. When in the engaged position, the seat applicator 400, the front applicator 500, and the rear applicator 600 are configured to deliver the HIFEM and RF energies to the patient's pelvic floor muscles for treating the patient's hypogonadism. As a result, the device 100 may further be used to treat a patient for erectile dysfunction and premature ejaculation.

Figure 3:
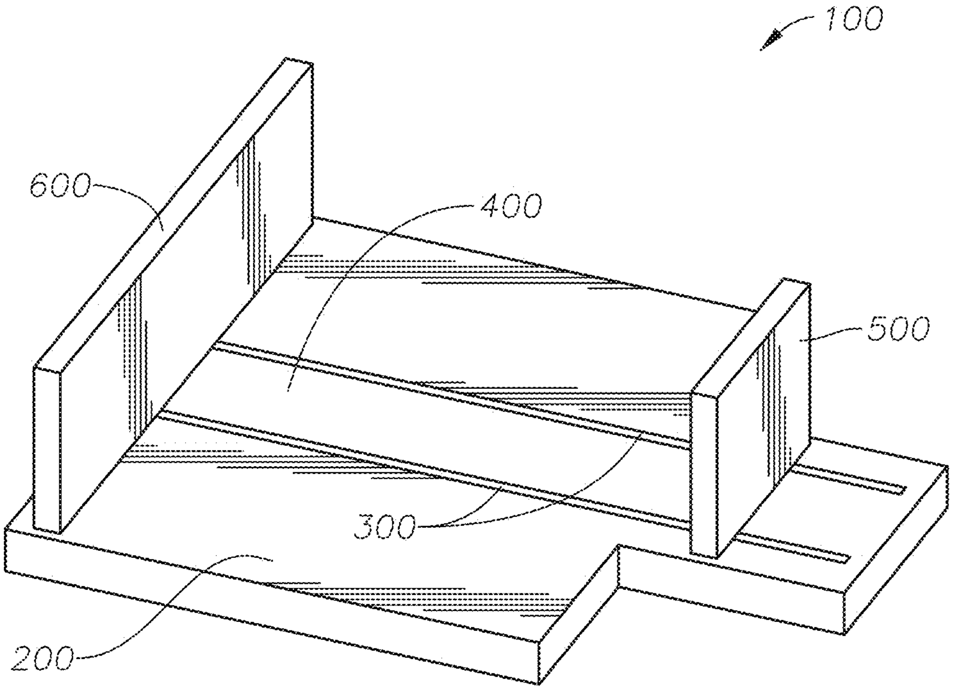
FIG. 3 is a side view of the device for treating hypogonadism using HIFEM/RF energies, with a front applicator in an engaged position, according to an embodiment.
Figure 4:
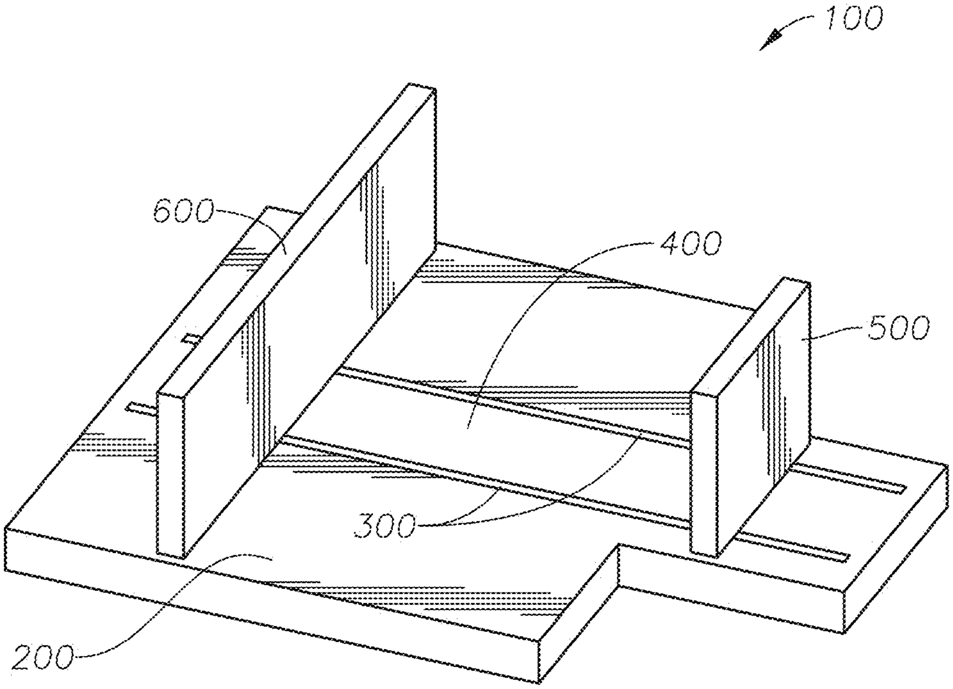
FIG. 4 is a side view of the device for treating hypogonadism using HIFEM/RF energies, with a front applicator and a rear applicator in an engaged position, according to an embodiment.

FIG. 3 is a side view of the device 100 for treating hypogonadism using HIFEM/RF energies, with a front applicator 500 in an engaged position, according to an embodiment. As shown in FIG. 3, the front applicator 500 is configured to slide forward towards the patient until it engages the patient's penis and the front portion of the patient's pelvic floor. FIG. 4 is a side view of the device 100 for treating hypogonadism using HIFEM/RF energies, with a front applicator 500 and a rear applicator 600 in an engaged position, according to an embodiment. As shown in FIG. 4, the rear applicator 600 is configured to also slide forward towards the patient, until it engages the patient's anus and the rear portion of the patient's pelvic floor.

Figure 5B:
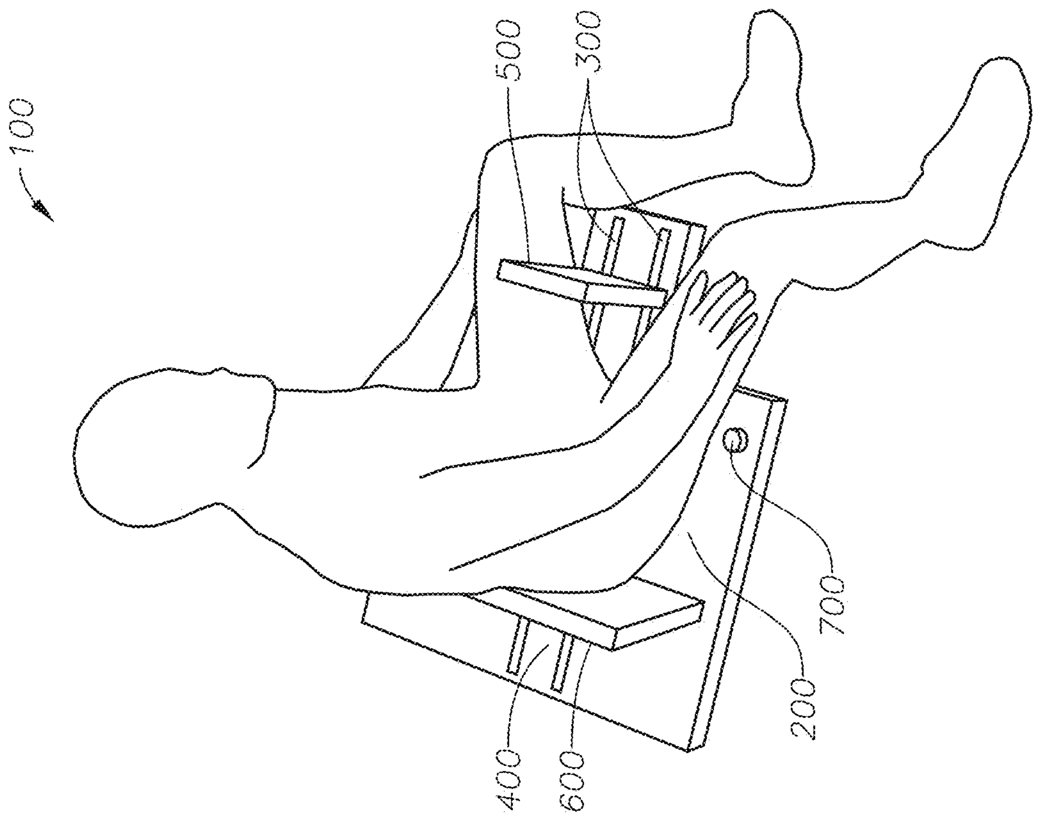
FIGS. 5A-5C illustrate the device for treating a patient experiencing hypogonadism using HIFEM/RF energies, according to embodiments.
Figure 5A:
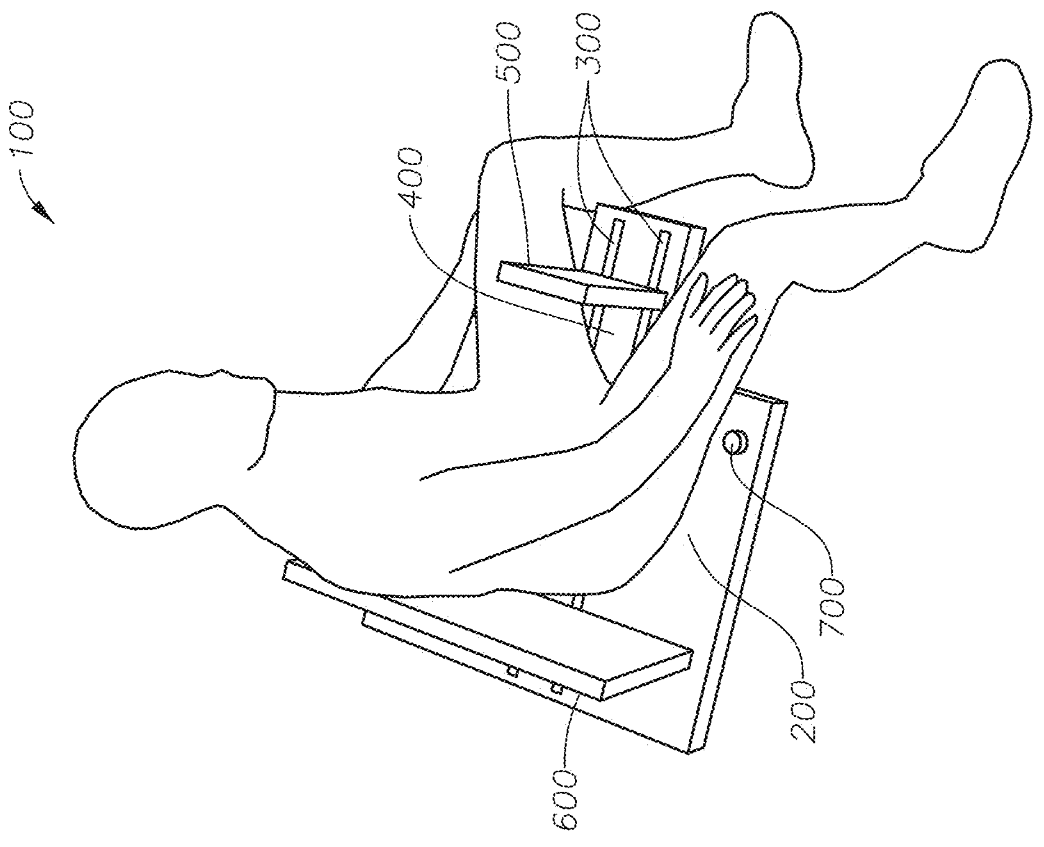
Figure 5C:
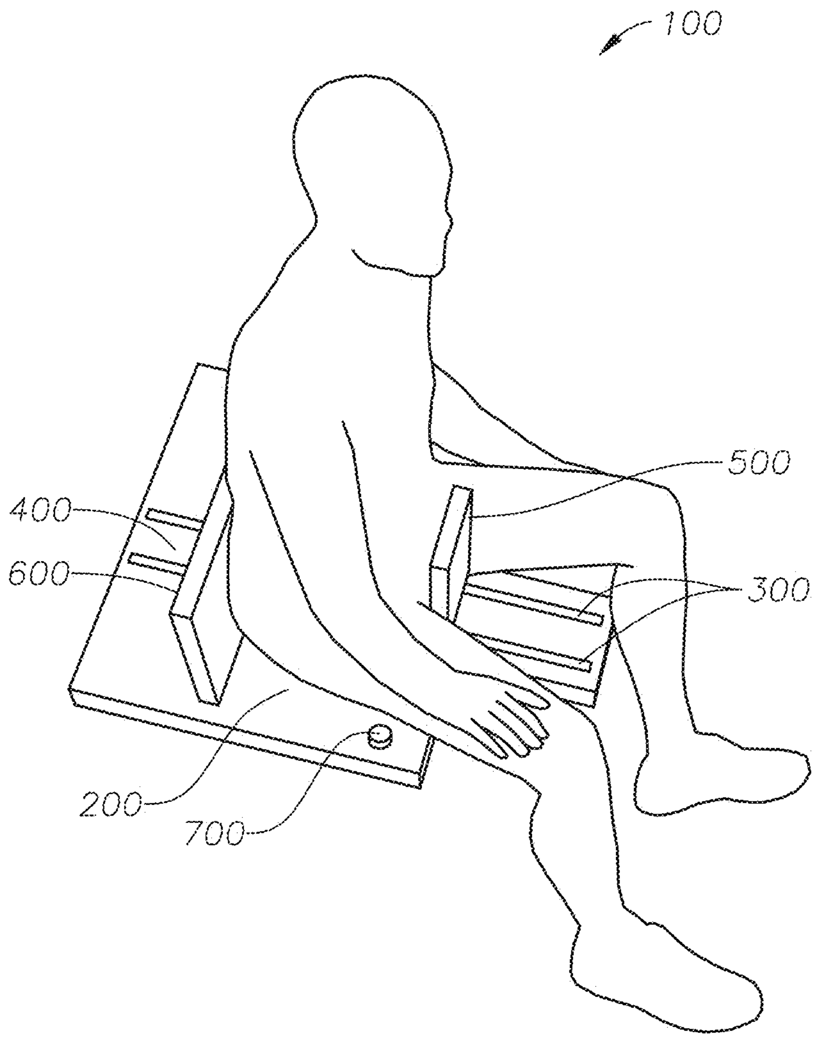

FIGS. 5A-5C illustrate the device 100 for treating a patient experiencing hypogonadism using HIFEM/RF energies, according to embodiments. FIG. 5A is a top view of the device 100 with the front applicator 500 and rear applicator 600 moving into an engaged position to the patient's body; FIG. 5B is a side view of the device 100 with the front applicator 500 moving into an engaged position to the patient's body and a rear applicator 600 engaged with the rear torso of the patient; FIG. 5C is a side view of the device 100 with the front applicator 500 and the rear applicator 600 fully engaged with the front and rear torso of the patient, according to an embodiment, respectively. Once the first applicator 500 and the rear applicator 600 are fully engaged, treatment with the HIFEM and RF energies can begin, as discussed in more detail below.

According to an embodiment, the front applicator 500 and the rear applicator 600 are designed to accommodate the contour of the male pelvic area. The front applicator 500 and the rear applicator 600 could be distinctly sized components that can be mixed and matched according to the patient's size and needs. The applicators' 400, 500, 600 primary objective is to strengthen the pelvic floor and increase blood flow to the testes, enhancing the environment for optimal testosterone synthesis. The ergonomic design of the applicators 500, 600 ensure accurate positioning, delivering focused electromagnetic waves to the testicular region and boosting testosterone. The device 100 is configurable to various HIFEM/RF machines, widening its therapeutic application spectrum.

As shown in FIGS. 5A-5*c*, the device 100 further includes a safety cutoff switch 700, operated by the patient, to modulate the treatment intensity within the tolerances of the patient's treatment comfort.

According to an embodiment, the HIFEM energy induces supramaximal contractions in the patient's pelvic floor muscles, enhancing testicular blood flow and stimulating natural testosterone synthesis. The RF energy complements the application of HIFEM energy by generating controlled heat within the tissues, which can aid in the reduction of excess adipose tissue and improve overall blood flow and tissue health. This thermal effect can help to remodel and tighten the tissues, potentially enhancing the treatment's efficacy in promoting testosterone production and improving the overall health of the pelvic region.

According to an embodiment, the device, as shown in FIGS. 1-4 and 5A-5C, further includes a monitor (not shown) configured to track the patient's comfort level during treatment and further configured to automatically adjust the intensity of the treatment based on real-time feedback from sensors or patient input, thereby optimizing the effectiveness of the treatment and improving patient comfort and ensuring that each patient receives the optimal treatment for his or her specific needs.

According to an embodiment, the device further includes a control panel (not shown) configured to allow an operator to control the device, adjust the settings of the HIFEM and RF energies, and monitor the progress of the treatment. The controller includes buttons, dials, and/or touchscreen controls for adjusting the intensity of the HIFEM and RF energies and a display for monitoring the treatment progress.

Figure 6:
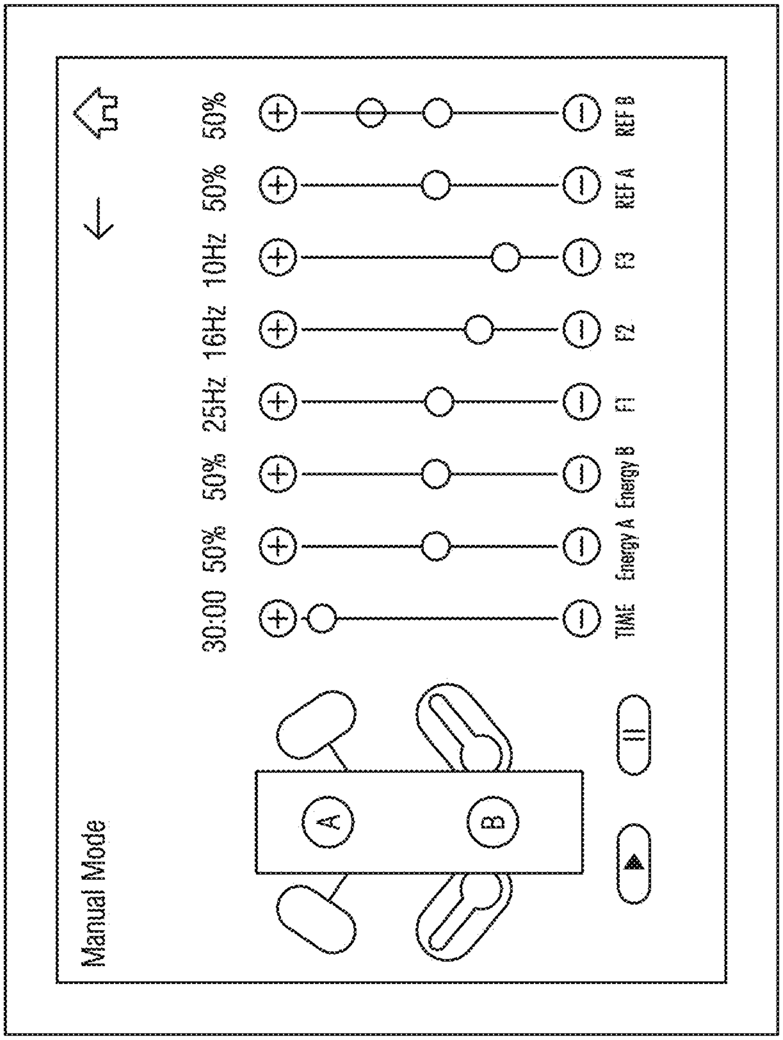
FIG. 6 illustrates a commercial HIFEM/RF machine configured to connect to the device for treating hypogonadism using HIFEM/RF energies, according to an embodiment.
Figure 7:
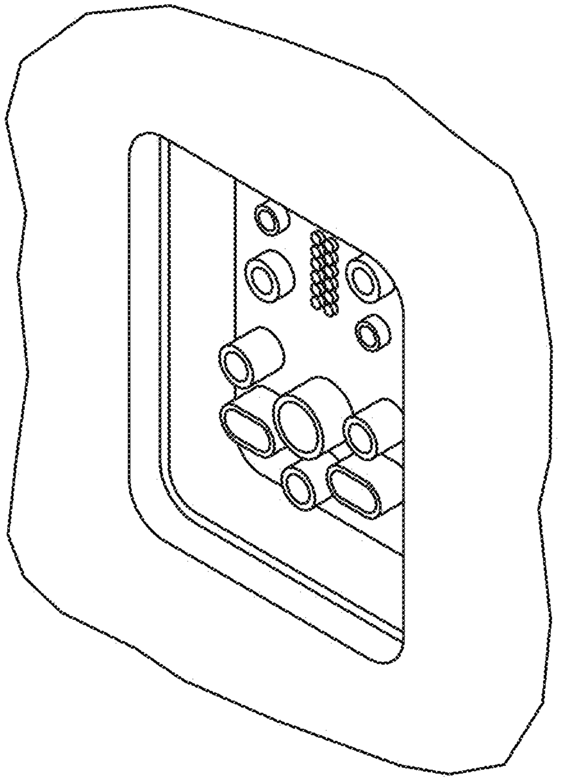
FIG. 7 illustrates a connection point on a commercial HIFEM/RF where a plug of the device is connected in operation, according to an embodiment.
Figure 8:
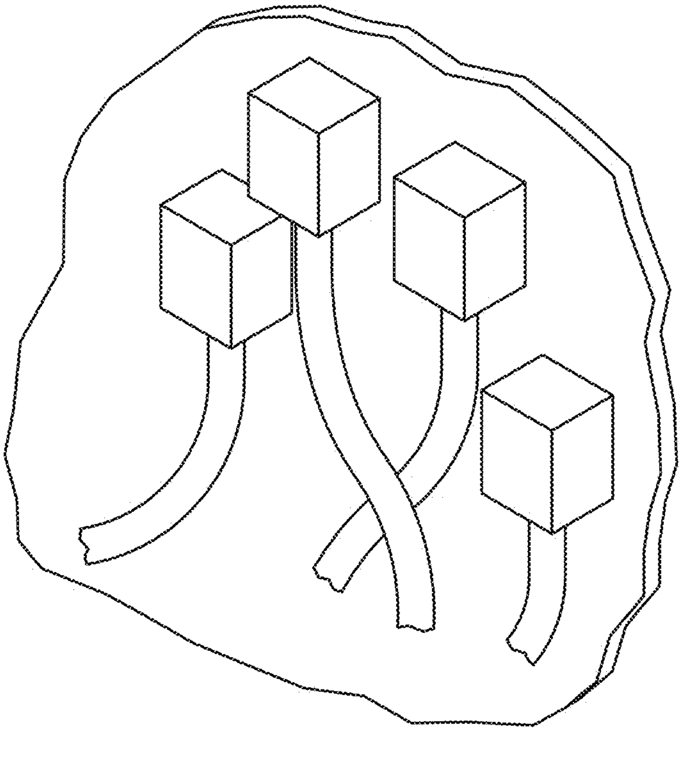
FIG. 8 illustrates a plug for a front applicator and a plug for a rear applicator connected with the commercial HIFEM/RF machine, according to an embodiment.

According to an embodiment, the device includes a HIFEM generator, as shown in FIGS. 6-8, a high-powered component that produces a high intensity focused electromagnetic field used in the HIFEM therapy. The HIFEM generator includes features for adjusting the intensity of the field, allowing the therapy to be customized for each patient.

According to an embodiment, the device includes a RF generator, as shown in FIGS. 6-8, a powerful component that produces the radio frequency used in RF therapy The RF generator includes features for adjusting the intensity of the field, allowing the therapy to be customized for each patient.

Figure 9:
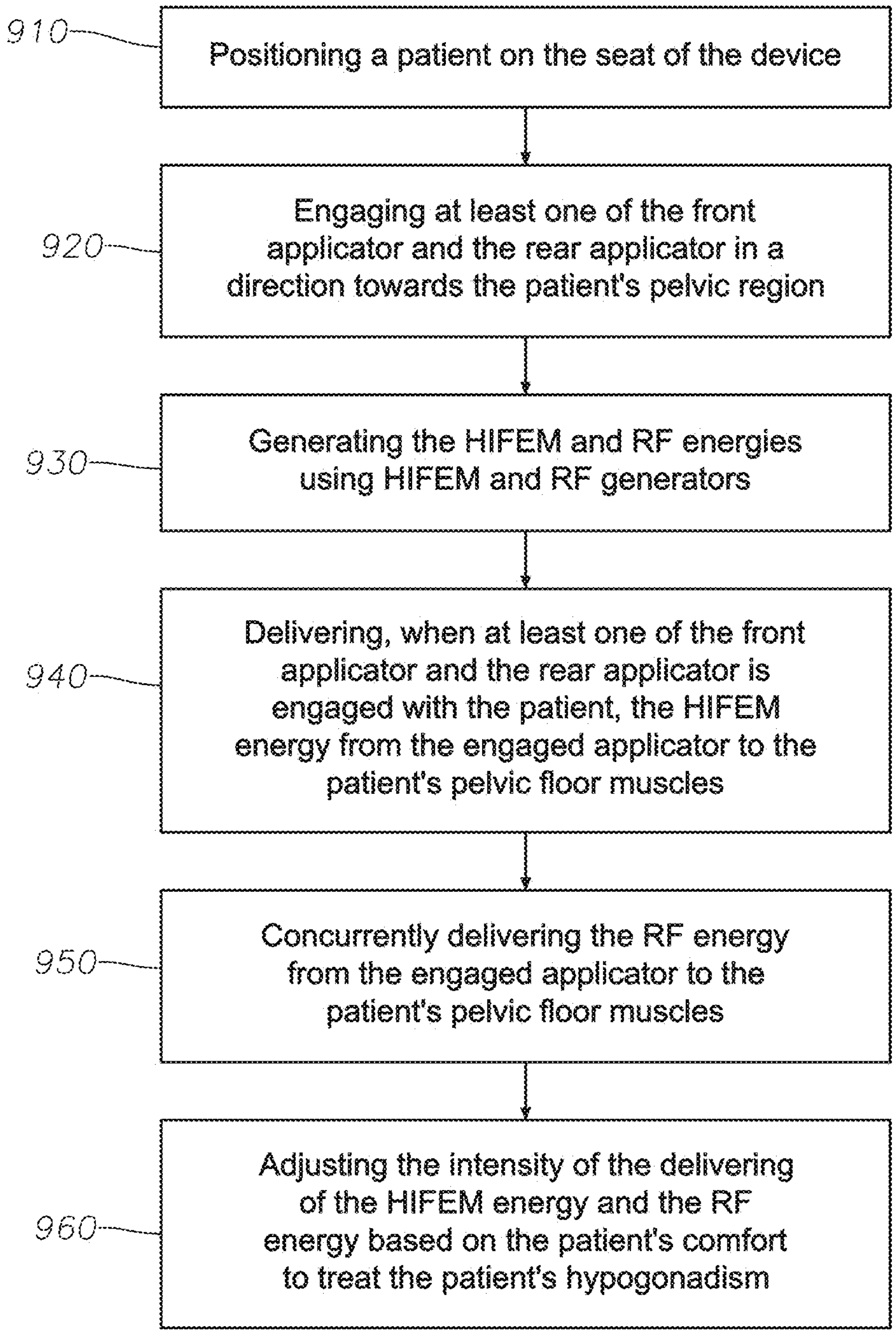
FIG. 9 illustrates a method for treating hypogonadism, according to an embodiment.

FIG. 9 illustrates a method for treating hypogonadism, according to an embodiment. The method for treating hypogonadism, the method using a device, including a seat, where the seat includes a pair of longitudinal grooves, and a pair of applicators. Each applicator is configured to deliver HIFEM energy and RF energy. The pair of longitudinal grooves are configured to engage the pair of applicators, where the applicators are slidably engaged to move along the longitudinal grooves from a disengaged position to an engaged position against a patient's body for treating hypogonadism. The pair of applicators includes a front applicator configured to engage a patient's penis and a front portion of the patient's pelvic floor and a rear applicator configured to engage a patient's anus and a rear portion of the patient's pelvic floor, in the engaged position. When in the engaged position, the front applicator and the rear applicator are configured to deliver the HIFEM and RF energies to the patient's pelvic floor muscles for treating the patient's hypogonadism.

The method includes the steps of positioning a patient on the seat of the device 910, engaging at least one of the front applicator and the rear applicator in a direction towards the patient's pelvic region 920, and generating the HIFEM and RF energies using HIFEM and RF generators 930. The method further includes the steps of delivering, when at least one of the front applicator and the rear applicator is engaged with the patient, the HIFEM energy from the engaged applicator to the patient's pelvic floor muscles 940, concurrently delivering the RF energy from the engaged applicator to the patient's pelvic floor muscles 950, and adjusting the intensity of the delivering of the HIFEM energy and the RF energy based on the patient's comfort to treat the patient's hypogonadism 960.

The method for treating hypogonadism according to an embodiment will now be described in more detail.

Initiation of Treatment: The method for treating hypogonadism, according to an embodiment, begins with the patient being properly fitted for the correct seat 200 and HIFEM/RF front and rear applicators 500, 600. The front and rear applicators 500, 600 are designed to comfortably accommodate the dimensions of the patient's pelvic region. The applicators 400, 500, 600 have a monochrome design with a contrasting outline that indicates the area where the HIFEM and RF energies are provided. This ensures that the patient can comfortably position themselves, while the energy is specifically directed towards the pelvic floor muscles and groin. The front and rear applicators 500, 600 are designed to accommodate the contour of the male pelvic area to ensure optimal contact with the patient's body.

Delivery of HIFEM Therapy: The method further includes the generation of HIFEM energy and delivery of the HIFEM energy via the seat applicator 400 and the front and rear applicators 500, 600 to the patient's pelvic floor muscles. HIFEM energy is crucial to the process for treating hypogonadism, according to an embodiment. The HIFEM energy operates by inducing supramaximal muscle contractions. When exposed to these strong contractions the muscle becomes stronger and larger. The intensity of the HIFEM field can be adjusted using the control panel, enabling the therapy to be customized for each patient. This ensures that each patient receives the optimal treatment for their specific needs, providing a more effective, comfortable, and clinically guided solution.

The HIFEM generator produces a high intensity focused electromagnetic field. The electromagnetic field is carefully directed toward the patient's pelvic floor muscles. The HIFEM energy induces supramaximal muscle contractions, which are impossible through voluntary contractions. When exposed to these strong contractions, the muscle tissue adapts to extreme conditions by remodeling its inner structure, resulting in muscle building and sculpting. In the context of hypogonadism treatment, the HIFEM energy targets and strengthens the pelvic floor muscles.

Delivery of RF Therapy: The method further includes the generation of RF energy and delivery of the RF energy via the seat applicator 400 and the front and rear applicators 500, 600 to the patient's pelvic floor muscles. The RF energy is another essential part of the treatment process. The RF generator produces a radio frequency, which is delivered by the seat applicator 400 and the front and rear applicators 500, 600 directly towards the fat tissues located in and around the patient's pelvic floor muscles. The RF energy generates heat through the oscillation of charged particles within the tissues, leading to thermal damage and subsequent reduction of fat cells. The heat generated by the RF energy increases the temperature of the fat cells, causing them to break down and be naturally eliminated by the body over time. In the context of hypogonadism treatment, the RF energy targets and reduces the fat tissues located in and around the patient's pelvic floor muscles. The intensity of the RF energy can be adjusted using the control panel, allowing the energy to be customized for each patient. This ensures that each patient receives the optimal treatment for their specific needs, providing a more effective, comfortable, and clinically guided solution.

According to an embodiment, a physician or medical practitioner is needed to properly fit the patient to the device seat 200, the seat applicator 400, the front applicator 500, and the rear applicator 600, to operate the device 100, and to monitor the application of the HIFEM energy and the RF energy, to ensure proper delivery of the HIFEM and RF energies to the patient for treatment.

In summary, the RF energy delivered by the device provides a non-invasive, targeted, and effective method for reducing fat in the patient's pelvic floor muscles, thereby addressing another key factor contributing to hypogonadism. By combining the RF energy with the HIFEM energy, the device offers a comprehensive and innovative solution for treating hypogonadism.

In practice, the physician or medical practitioner increases or decreases the intensity of the HIFEM energy and the RF energy delivered to the patient to maximize the energy delivered up to the point of patient comfort because more energy will make for more effective treatments. The physician or medical practitioner should ask the patient to indicate if each power level is comfortable or uncomfortable, gradually increasing or decreasing the intensity of the delivered the HIFEM energy and the RF energy according to the patient's response. The HIFEM energy causes muscle contractions and the physician or medical practitioner should ask if the contractions are comfortable or uncomfortable. The RF energy is warm when applied, and the physician or medical practitioner should ask if the temperature felt by the patient is comfortable or uncomfortable. Energy should be increased up to the point of comfort for HIFEM muscle contractions and RF temperature tolerance.

As the patient's muscles become stronger and the tissue around the pelvic floor adapts to the treatment, the physician or medical practitioner can gradually increase the intensity of the HIFEM energy and the RF energy. This progressive approach allows the muscles to adapt to the increased stimuli without causing undue strain or discomfort. The customization of the method according to embodiments ensures that each patient receives the optimal treatment for their specific needs, providing a more effective, comfortable, and convenient solution for hypogonadism. In summary, the HIFEM energy delivered by the device provides a non-invasive, targeted, and effective method for strengthening the patient's pelvic floor muscles, thereby addressing one of the key factors contributing to hypogonadism.

According to an embodiment, the HIFEM energy and the RF energy are concurrently applied to the patient's pelvic floor muscles using the front, bottom, and rear applicators. The HIFEM energy is pulsed at between 1 Hz to 500 Hz with a continuous application of RF energy in the range of 1 MHz to 3 MHz. The initial application of HIFEM energy is applied for 5 seconds, followed by a 3-second rest, with a total treatment of 10-30 minutes. The RF energy, if used, is applied to the patient's pelvic floor muscles to the point the patient experiences a sensation of warmth near the applicator that is comfortable. Longer treatments may be applied, depending on the patient's comfort level.

The patient's treatment progress is meticulously tracked over multiple treatment sessions. Utilizing advanced algorithms, the device analyzes various parameters and adapts the intensity of the treatments accordingly. These adjustments are based on user comfort.

Completion of Treatment: The method for treating hypogonadism is completed when 30 minutes of treatment has lapsed, or when the physician or medical practitioner determines that the patient is no longer able to comfortably tolerate treatment. Upon completion of a treatment session, the device automatically shuts off the HIFEM and RF generators and terminates delivery of the HIFEM and RF energies to the patient, ensuring the patient's safety. The patient is then carefully assisted from the seat of the device. It is important to ensure that the patient is feeling well and not experiencing any discomfort or adverse effects from the treatment, before having the patient stand. The patient is observed for a short post-treatment period, for example, 15 minutes, under the physician's or medical practitioner's supervision. This observation period is crucial to monitor the patient for any immediate adverse reactions or complications that may arise from the treatment. During this time, the physician or medical practitioner can answer any of patient's questions about the treatment, discuss the patient's experience, and provide further instructions for post-treatment care.

Post-treatment care instructions are provided to the patient, including staying hydrated, maintaining a healthy diet, and engaging in regular physical activity to support the treatment's muscle strengthening and fat reduction effects. The patient is also advised to monitor their sleep and breathing patterns and report any significant changes to their physician.

If the patient feels well and shows no signs of adverse reactions, they are released to return home. The patient is advised to contact their healthcare provider if they experience discomfort or unusual symptoms following the treatment. This post-treatment observation and care are essential components of patient safety and satisfaction, contributing to the overall effectiveness of the treatment process.

The seat 200 and the front and rear applicators 600, 600 should be cleaned and disinfected in preparation for the next patient, ensuring the highest hygiene and patient safety standards.

The patient's progress is tracked over multiple treatment sessions. The intensity of the treatments may be adjusted based on the patient's comfort.

Upon completion of the treatment course, the patient's condition is re-evaluated. If the treatment has improved the patient's sexual function, follow-up treatments may be scheduled as needed to maintain the results. If the patient's symptoms have not improved significantly, alternative treatment options may be explored. In all cases, the goal is to provide a safe, comfortable, and effective treatment for the patient's erectile dysfunction and premature ejaculation, thereby enhancing the patient's sexual function and overall quality of life.

Embodiments provided a customized treatment based on the patient's needs. The customized treatment includes delivering HIFEM and RF energies to a patient using ergonomically designed applicators contoured to a patient's pelvic area with the ability to adjust the intensity of the HIFEM and RF energies according to the patient's comfort level to ensure accurate positioning and delivery of focused electromagnetic waves to the patient's testicular region to boost testosterone, and thereby treat the patient's hypogonadism.

Embodiments provide a device for treating hypogonadism including safety measures, such as a button for the patient or physician or medical practitioner to press if the temperature or intensity of the muscle contractions is too great for the patient's comfort, and a protocol for observing the patient post-treatment to ensure their safety.

Embodiments provide a method for treating hypogonadism that progressively apply treatment at very low, safe levels of energy and gradually increase those levels from treatment to treatment, thereby considering the patient's comfort and the progressive strengthening of the muscles' contractions.

The device and the method are designed for use in a clinical setting under the supervision of a trained healthcare professional to ensure the safety and effectiveness of the treatment. By addressing the root causes of hypogonadism, the device and the method can treat a patient's erectile dysfunction and premature ejaculation, resulting in improvements to overall health and well-being.

The device and the method offer cost-effective solutions for hypogonadism treatment, reducing the need for ongoing treatments or interventions, and thereby leading to significant cost savings for patients and healthcare providers.

The device is easy to use and the method is easy to perform, utilizing a user-friendly control panel and clear instructions for positioning and operating the device, thereby making it accessible for a wide range of healthcare providers and patients.

According to various embodiments, the device and the method can also be simplified and used within a patient's home. The in-home device includes user-friendly controls and safety features, enabling a patient to apply treatment in the comfort of their home. In-home treatment would include the guidance of a healthcare provider.

According to an embodiment, the device could be configured as a portable device for easy transport and use in various settings. A portable device is particularly useful for patients who travel frequently or for healthcare providers offering mobile services.

According to an embodiment, the device could be operated wirelessly, eliminating the need for a power cord and increasing the ease of use and portability.

According to an embodiment, the device could be integrated with virtual or augmented reality technology to provide visual feedback or guidance during treatment, enhancing the patient experience and potentially improving treatment outcomes.

According to an embodiment, the device and method could incorporate artificial intelligence algorithms to optimize treatment parameters based on individual patient data, potentially improving the effectiveness and efficiency of the treatment.

According to an embodiment, the device and method could be modified to treat conditions related to weakened pelvic floor muscles or excessive fat in the pelvic area. For example, they could be used for specific conditions related to sexual dysfunction or urinary incontinence.

According to an embodiment, while the present device and method utilize HIFEM and RF therapies, alternative versions could incorporate other therapies, such as ultrasound or laser therapy, to stimulate muscles and reduce fat.

According to an embodiment, the device may further include diagnostic tools like sensors monitoring muscle strength or fat distribution in the pelvic area, offering real-time feedback on treatment effectiveness.

According to an embodiment, the device could be accompanied by various applicator sizes and shapes to fit different anatomical features. It could also include applicators intended for different body parts or custom-made applicators based on individual patient measurements. This would allow for a greater range of customization and could improve the comfort and effectiveness of the treatment.

According to an embodiment, the device and method could be configured to use only RF energy to reduce fat in the patient's pelvic area, thereby simplifying the device, reducing cost of the device.

According to an embodiment, the device could be configured to use only HIFEM energy to strengthen the patient's pelvic floor muscles, thereby simplifying the device and reducing cost of the device, and addressing the patient's need to strengthen muscles.

According to an embodiment, the device could be configured such that the HIFEM and RF generators are separate modules that can be added or removed, as needed. This would allow for a high degree of customization and could make the device more adaptable to the needs of different patients.

According to an embodiment, the device could include a set of interchangeable applicators of different sizes and shapes, further enabling customization of the device to accommodate different patients' anatomies and improving the comfort and effectiveness of the treatment.

Embodiments provide non-obvious advantages over conventional devices and treatments for hypogonadism:

The device and method for treating hypogonadism are a non-invasive solution for erectile dysfunction and premature ejaculation, thereby avoiding the need for surgical interventions or discomforting devices that must be worn.

The device and method for treating hypogonadism provide a combined application of HIFEM and RF therapies efficiently strengthening the pelvic floor muscles and reducing fat tissues in and around the patient's pelvic floor muscles. This dual treatment approach addresses the root causes of erectile dysfunction and premature ejaculation, leading to significant improvement in symptoms.

The design of the device, including the pelvic rest with integrated HIFEM/RF front and back applicators, ensures a comfortable experience for the patient during treatment. The patient can rest their pelvic area on the applicator, and the intensity of the energies can be adjusted to accommodate the patient's comfort level.

The device and method for treating hypogonadism allow personalized treatment based on each patient's needs. The intensity of the HIFEM and RF energies can gradually escalate over time as the patient's muscles become stronger, ensuring optimal results.

The device and method for treating hypogonadism are designed for use in a clinical setting, under the supervision of a trained healthcare professional. This ensures the safety and effectiveness of the treatment.

By addressing the root causes of erectile dysfunction and premature ejaculation, the device and method for treating hypogonadism can significantly improve the sexual performance of patients, thereby improving overall health, well-being, and personal relationships.

The device and method for treating hypogonadism offer a cost-effective solution for treating erectile dysfunction and premature ejaculation. By reducing the need for ongoing treatments or interventions, the device and method can lead to significant cost savings for patients and healthcare providers.

The device and method for treating hypogonadism are user-friendly, with a straightforward control panel and clear instructions for positioning and use. This makes it accessible for a wide range of healthcare providers and patients.

While preferred embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that any claims presented define the scope of the various embodiments and that methods and structures within the scope of these claims and their equivalents be covered thereby.

Embodiments described herein, therefore, are well adapted to carry out the objects and attain the ends and advantages mentioned, as well as others inherent therein. While a presently preferred embodiment has been given for purposes of disclosure, numerous changes exist in the details of procedures for accomplishing the desired results. These and other similar modifications will readily suggest themselves to those skilled in the art, and are intended to be encompassed within the spirit of the various embodiments disclosed herein and the scope of the appended claims.

Although the various embodiments have been described in detail, it should be understood that various changes, substitutions, and alterations can be made hereupon without departing from the principle and scope of the various embodiments. Accordingly, the scope of the various embodiments should be determined by the following claims and their appropriate legal equivalents.

The singular forms "a," "an," and "the" include plural referents, unless the context clearly dictates otherwise.

Optional or optionally means that the subsequently described event or circumstances can or may not occur. The description includes instances where the event or circumstance occurs and instances where it does not occur.

Ranges can be expressed herein as from about one particular value, and/or to about another particular value. When such a range is expressed, it is to be understood that another embodiment is from the one particular value and/or to the other particular value, along with all combinations within said range.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that the mere use of the term "first" and "second" does not require that there be any "third" component, although that possibility is contemplated under the scope of the various embodiments.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The embodiments can suitably comprise, consist or consist essentially of the elements disclosed and can be practiced in the absence of an element not disclosed.

What is claimed is:

1. A device for treating hypogonadism, comprising:

a seat, the seat comprising a pair of longitudinal grooves; and a pair of applicators, wherein each applicator is configured to deliver High-Intensity Focused Electromagnetic Technology (HIFEM) energy and Radio Frequency (RF) energy, wherein the pair of longitudinal grooves are configured to engage the pair of applicators, the applicators slidably engaged to move along the longitudinal grooves from a disengaged position to an engaged position against a patient's body for treating hypogonadism, wherein the pair of applicators comprises a front applicator configured to engage a patient's penis and a front portion of the patient's pelvic floor and a rear applicator configured to engage a patient's anus and a rear portion of the patient's pelvic floor, in the engaged position, and wherein, when in the engaged position, the front applicator and the rear applicator are configured to deliver the HIFEM and RF energies to the patient's pelvic floor muscles for treating the patient's hypogonadism.

2. The device of claim 1, wherein the seat further comprises a seat applicator, the seat applicator being configured to deliver HIFEM and RF energies.

3. The device of claim 2, wherein, when the device is in the engaged position, the seat applicator is configured to deliver the HIFEM and RF energies to the patient's pelvic floor muscles for treating the patient's hypogonadism.

4. The device of claim 3, wherein the seat applicator, the front applicator and the rear applicator are each configured to deliver the HIFEM and RF energies concurrently to the muscles and fat tissues of the patient's pelvic floor muscles.

5. The device of claim 4, wherein the seat applicator, the front applicator, and the rear applicator are each configured to concurrently deliver the HIFEM energy pulsed at between 1 Hz to 500 Hz with a continuous application of RF energy in the range of 1 MHz to 3 MHz.

6. The device of claim 4, wherein the seat applicator, the front applicator, and the rear applicator are each configured to deliver the HIFEM energy and RF energy for a duration of 10 to 30 minutes long, depending on the patient's comfort level.

7. The device of claim 1, further comprising:
- a control panel comprising a patient-operated button configured to terminate the delivery of the HIFEM and RF energies, when the patient experiences discomfort during treatment.

8. The device of claim 1, wherein the front applicator and the rear applicator are designed to accommodate the contour of the male pelvic area, ensuring accurate positioning and delivery of focused electromagnetic waves to the patient's testicular region and boosting testosterone.

9. A method for treating hypogonadism, the method using a device, comprising:
- a seat, the seat comprising a pair of longitudinal grooves; and
- a pair of applicators,
- wherein each applicator is configured to deliver High-Intensity Focused Electromagnetic Technology (HIFEM) energy and Radio Frequency (RF) energy,
- wherein the pair of longitudinal grooves are configured to engage the pair of applicators, the applicators slidably engaged to move along the longitudinal grooves from a disengaged position to an engaged position against a patient's body for treating hypogonadism,
- wherein the pair of applicators comprises a front applicator configured to engage a patient's penis and a front portion of the patient's pelvic floor and a rear applicator configured to engage a patient's anus and a rear portion of the patient's pelvic floor, in the engaged position, and
- wherein, when in the engaged position, the front applicator and the rear applicator are configured to deliver the HIFEM and RF energies to the patient's pelvic floor muscles for treating the patient's hypogonadism
- the method comprising the steps of:
- positioning a patient on the seat of the device;
- engaging at least one of the front applicator and the rear applicator in a direction towards the patient's pelvic region;
- generating the HIFEM and RF energies using HIFEM and RF generators;
- delivering, when at least one of the front applicator and the rear applicator is engaged with the patient, the HIFEM energy from the engaged applicator to the patient's pelvic floor muscles;
- concurrently delivering the RF energy from the engaged applicator to the patient's pelvic floor muscles; and
- adjusting the intensity of the delivering of the HIFEM energy and the RF energy based on the patient's comfort to treat the patient's hypogonadism.

10. The method of claim 9, further comprising the steps of:
- engaging the other of the front applicator and the rear applicator in a direction towards the patient's pelvic region;
- generating the HIFEM and RF energies using HIFEM and RF generators;
- delivering, when the other of the front applicator and the rear applicator is engaged with the patient, the HIFEM energy from the other engaged applicator to the patient's pelvic floor muscles;
- concurrently delivering the RF energy from the other engaged applicator to the patient's pelvic floor muscles; and
- adjusting the intensity of the delivering of the HIFEM energy and the RF energy based on the patient's comfort to treat the patient's hypogonadism.

11. The method of claim 9, wherein the seat further comprises a seat applicator, the seat applicator being configured to deliver HIFEM and RF energies,
- the method further comprising the steps of:
- delivering, from the seat applicator, the HIFEM energy to the patient's pelvic floor muscles;
- concurrently delivering the RF energy from the seat applicator to the patient's pelvic floor muscles; and
- adjusting the intensity of the delivering of the HIFEM energy and the RF energy based on the patient's comfort to treat the patient's hypogonadism.

12. The method of claim 11, wherein the seat applicator, the front applicator, and the rear applicator are each configured to concurrently deliver the HIFEM energy pulsed at between 1 Hz to 500 Hz with a continuous application of RF energy in the range of 1 MHz to 3 MHz.

13. The method of claim 12, wherein the seat applicator, the front applicator, and the rear applicator are each configured to deliver the HIFEM energy and RF energy for a duration of 10 to 30 minutes long, depending on the patient's comfort level.

14. The method of claim 9, wherein the delivering comprises delivering the HIFEM and RF energies concurrently to the muscles and fat tissues of the patient's pelvic floor muscles.

15. The method of claim 9, wherein the device further comprises a control panel comprising a patient-operated button,
- the method further comprising the step of:
- terminating, using the patient-operated button, the delivery of the HIFEM and RF energies, when the patient experiences discomfort during treatment.

16. The method of claim 9, wherein the front applicator and the rear applicator are designed to accommodate the contour of the male pelvic area, ensuring accurate positioning and delivery of focused electromagnetic waves to the patient's testicular region and boosting testosterone.

* * * * *